(12) United States Patent
Kolanko et al.

(10) Patent No.: US 8,092,020 B2
(45) Date of Patent: Jan. 10, 2012

(54) METHOD FOR DIAGNOSING A DISEASE STATE USING OCULAR CHARACTERISTICS

(76) Inventors: Christopher J. Kolanko, Morgantown, WV (US); Lance R. Molnar, Wheeling, WV (US)

( * ) Notice: Subject to any disclaimer, the term of this patent is extended or adjusted under 35 U.S.C. 154(b) by 0 days.

(21) Appl. No.: 12/718,342

(22) Filed: Mar. 5, 2010

(65) Prior Publication Data
US 2011/0172555 A1    Jul. 14, 2011

Related U.S. Application Data

(62) Division of application No. 10/740,979, filed on Dec. 19, 2003, now Pat. No. 7,703,918.

(60) Provisional application No. 60/434,976, filed on Dec. 19, 2002.

(51) Int. Cl.
A61B 3/10  (2006.01)
A61B 3/14  (2006.01)
A61B 3/00  (2006.01)

(52) U.S. Cl. ................ 351/205; 351/206; 351/246
(58) Field of Classification Search .......... 351/200–246; 435/6, 18, 28, 7.5, 7.95
See application file for complete search history.

(56) References Cited

U.S. PATENT DOCUMENTS

| | | |
|---|---|---|
| 4,850,691 A | 7/1989 | Gardner et al. |
| 4,993,825 A | 2/1991 | Abe et al. |
| 5,125,730 A | 6/1992 | Taylor et al. |
| 5,583,795 A | 12/1996 | Smyth |
| 5,778,893 A | 7/1998 | Potter |
| 6,022,109 A | 2/2000 | Dal Santo |
| 6,162,186 A * | 12/2000 | Scinto et al. .................. 600/558 |
| 6,260,968 B1 | 7/2001 | Stark et al. |
| 6,305,804 B1 | 10/2001 | Rice et al. |
| 6,382,792 B1 | 5/2002 | Khoury et al. |
| 6,387,618 B1 | 5/2002 | Kolanko et al. |
| 6,477,394 B2 | 11/2002 | Rice et al. |
| 6,544,193 B2 | 4/2003 | Abreu |
| 6,547,394 B2 | 4/2003 | Doherty |
| 6,565,210 B2 * | 5/2003 | Kobayashi et al. ........... 351/214 |
| 6,626,537 B1 | 9/2003 | Odom et al. |
| 6,631,989 B2 | 10/2003 | Odom et al. |
| 6,637,885 B2 | 10/2003 | Petrali |

(Continued)

FOREIGN PATENT DOCUMENTS
WO    WO-2004/056278 A2    7/2004

OTHER PUBLICATIONS

International Search Report for PCT/US03/41220, dated Oct. 5, 2004.

(Continued)

Primary Examiner — Mohammed Hasan
(74) Attorney, Agent, or Firm — Patton Boggs LLP

(57) ABSTRACT

A method for diagnosing a disease state in a subject, including examining the subject's eyes in order to determine whether the subject exhibits one or more symptoms of the disease state. Symptoms of the disease state include altered ocular characteristics, such as pupil size, pupil motility, ocular blood vessel coloration, and strobe light cutoff frequency. By evaluating changes to ocular characteristics, a disease state can be diagnosed in a subject. In addition, the severity of the disease state also can be determined.

13 Claims, 8 Drawing Sheets
(1 of 8 Drawing Sheet(s) Filed in Color)

U.S. PATENT DOCUMENTS

| | | |
|---|---|---|
| 7,204,590 B1 | 4/2007 | Lenoir |
| 7,703,918 B2 | 4/2010 | Kolanko et al. |
| 7,854,511 B2 * | 12/2010 | Molnar et al. ............... 351/221 |
| 2001/0055095 A1 | 12/2001 | D'Souza et al. |
| 2002/0024633 A1 | 2/2002 | Kim et al. |
| 2002/0047989 A1 | 4/2002 | Shibata |
| 2002/0171805 A1 | 11/2002 | Odom et al. |
| 2004/0207811 A1 | 10/2004 | Elsner |
| 2005/0057721 A1 | 3/2005 | Kolanko et al. |
| 2006/0146284 A1 | 7/2006 | Collins et al. |
| 2008/0212026 A1 | 9/2008 | Molnar et al. |

OTHER PUBLICATIONS

International Search Report and Written Opinion for PCT/US07/077739, dated Aug. 20, 2008.

International Search Report and Written Opinion for PCT/US08/78573, dated Dec. 2, 2008.

* cited by examiner

METHOD FOR DIAGNOSING A DISEASE STATE USING OCULAR CHARACTERISTICS

RELATED APPLICATIONS

This application is a divisional application of U.S. patent application Ser. No. 10/740,979, filed Dec. 19, 2003, now U.S. Pat. No. 7,703,918 B2, which claims priority to U.S. Provisional Application No. 60/434976 filed Dec. 19, 2002.

This invention was made in part with government support under contract number DAAH01-02-C-R171 awarded by the Defense Advanced Research Projects Agency (DARPA). The government may have certain rights in the invention.

BACKGROUND OF THE INVENTION

1. Field of the Invention

This invention relates to ocular characteristics and their role in assessing physical well-being and diagnosing the existence and severity of a disease state.

2. Related Art

The use of chemical and biological agents is an ever-increasing threat to people of all nations. In order to properly treat those who have been exposed to biological or chemical weapons, a rapid diagnosis is imperative. Additionally, in instances where there have been mass casualties as a result of exposure to chemical agents or biological toxins, there is a need for a system of rapidly assessing the severity of each individual's exposure in order to determine the requirements for appropriate treatment.

Due to the interconnection between the eyes and the various physiological systems of the body (e.g., cardiovascular, musculoskeletal, lymphatic, etc.), the eyes may be a key to rapidly diagnosing disease states, including biological toxin or chemical agent exposure. U.S. Pat. No. 6,305,804 issued to Rice et al. discloses a method for detecting the concentration of blood components, such as hemoglobin, glucose, and bilirubin. While this information may be useful to a person already diagnosed with a disease state, i.e., diabetes, for monitoring his or her glucose levels, or to diagnose jaundice in an infant, it does not provide a method for diagnosing any other disease states, such as exposure to chemical agents or biological toxins. Likewise, Rice et al. does not disclose a method for assessing the severity of exposure to such an agent or toxin.

U.S. Pat. No. 6,626,537 issued to Odom et al. discloses a method for monitoring a medical condition by analyzing light reflected back from a subject's eyes. Using the method taught by Odom et al., it may be possible to determine whether an abnormality exists in the patient's eyes. However, Odom does not teach a method for identifying, i.e., diagnosing, an unknown disease state. Nor does Odom teach a method for assessing the severity of a disease state previously identified. Odom et al. therefore does not provide a method for diagnosing and evaluating the severity of exposure to a biological toxin or chemical agent. There thus remains a need for a real-time, non-invasive method for diagnosing not only the existence of a disease state but also the severity, thereby allowing treatment strategies to be prioritized with respect to need, especially in situations involving mass casualties.

SUMMARY OF THE INVENTION

The present invention solves the foregoing problems by providing a non-invasive real-time method for diagnosing a disease state in a subject based upon ocular characteristics. Through temporal assessment of ocular characteristics, the existence and severity of a disease state can be diagnosed.

One aspect of the invention is a method of diagnosing a disease state in a subject, including the steps of examining the subject's eye in order to determine whether the subject exhibits an ocular characteristic of the disease state, and if so, evaluating the ocular characteristic in order to diagnose the disease state, including its severity.

Another aspect of the invention is a method of diagnosing cyanide exposure of a subject, including the step of determining whether the subject's ocular blood vessel coloration varies significantly from a normal ocular blood vessel coloration.

Another aspect of the invention is a method of diagnosing carbon monoxide exposure of a subject, including the step of determining whether the subject's ocular blood vessel coloration varies significantly from normal ocular blood vessel coloration.

Another aspect of the invention is a method of diagnosing *botulinum* toxin exposure of a subject, including the step of determining whether the subject's strobe cutoff frequency varies significantly from a normal strobe cutoff frequency.

Another aspect of the invention is a method of diagnosing exposure to a chemical agent or a biological toxin, including the steps of evaluating a primary ocular characteristic to determine whether there has been exposure to the chemical agent or biological toxin, and evaluating a secondary ocular characteristic to determine to what extent the subject was exposed to the chemical agent or biological toxin.

A feature of the invention is a method for diagnosing a disease state in a subject based upon altered ocular characteristics in the subject.

An advantage of the invention is that the eye examination can be performed non-invasively.

Another advantage of the invention is that ocular characteristics can be used to rapidly and accurately diagnose individuals who have been exposed to chemical agents or biological toxins, including but not limited to: organophosphate compounds (anti-cholinesterases), cyanide compounds, carbon monoxide, and *botulinum* toxin.

Another advantage of the invention is that it provides a real-time assessment which may serve as an early-warning system for possible complications based upon generalized information obtained from ocular characteristics.

BRIEF DESCRIPTION OF THE DRAWINGS

The application contains at least one drawing executed in color. Copies of this patent or patent application publication with color drawing(s) will be provided by the Office upon request and payment of the necessary fee.

The present invention is described with reference to the accompanying drawings. In the drawings, like reference numbers indicate identical or functionally similar elements. Additionally, the left-most digit(s) of a reference number identifies the drawing in which the reference number first appears.

FIG. 10 is a concentration-response curve for fundal artery coloration changes in Sprague-Dawley rats in response to inhalational exposure to carbon monoxide gas for 60 minutes. Data was obtained 60 minutes after initiation of carbon monoxide administration except for one animal from the 2500 ppm group which expired prior to this time point. Data for this animal was obtained from images taken approximately 1 minute prior to respiration cessation (after 51 minutes of carbon monoxide inhalation). Extrapolated $EC_{50}$=289±37 ppm. Changes became statistically significant (p<0.05) at the 250 ppm for 60 minutes dose. Means have been normalized to the maximal observed change in all animals (38.5%) and error bars represent ±S.E.M.

FIG. 11 is a time-course plot for the occurrence of symptomology and death for Sprague-Dawley rats injected (I.P.) with varying doses of *botulinum* toxin. Data are plotted as means, error bars are omitted to simplify graph. Data points which had means of greater than 48 hours are not plotted. Y-axis ([*Botulinum* Toxin], pg/kg) is logarithmic and base-10 notation is used to indicate dose in picograms/kilogram. Loss of exploratory behavior was used for quantitation of general motor symptomology (see text). Significant (p<0.05) decrease in pupillary reflex to increased light intensity (compared to baseline) used to quantitate impaired pupillary reflex. Note: larger Y-axis values are at the bottom of the graph.

EMBODIMENTS OF THE INVENTION

Ocular Characteristics

Figure 1:
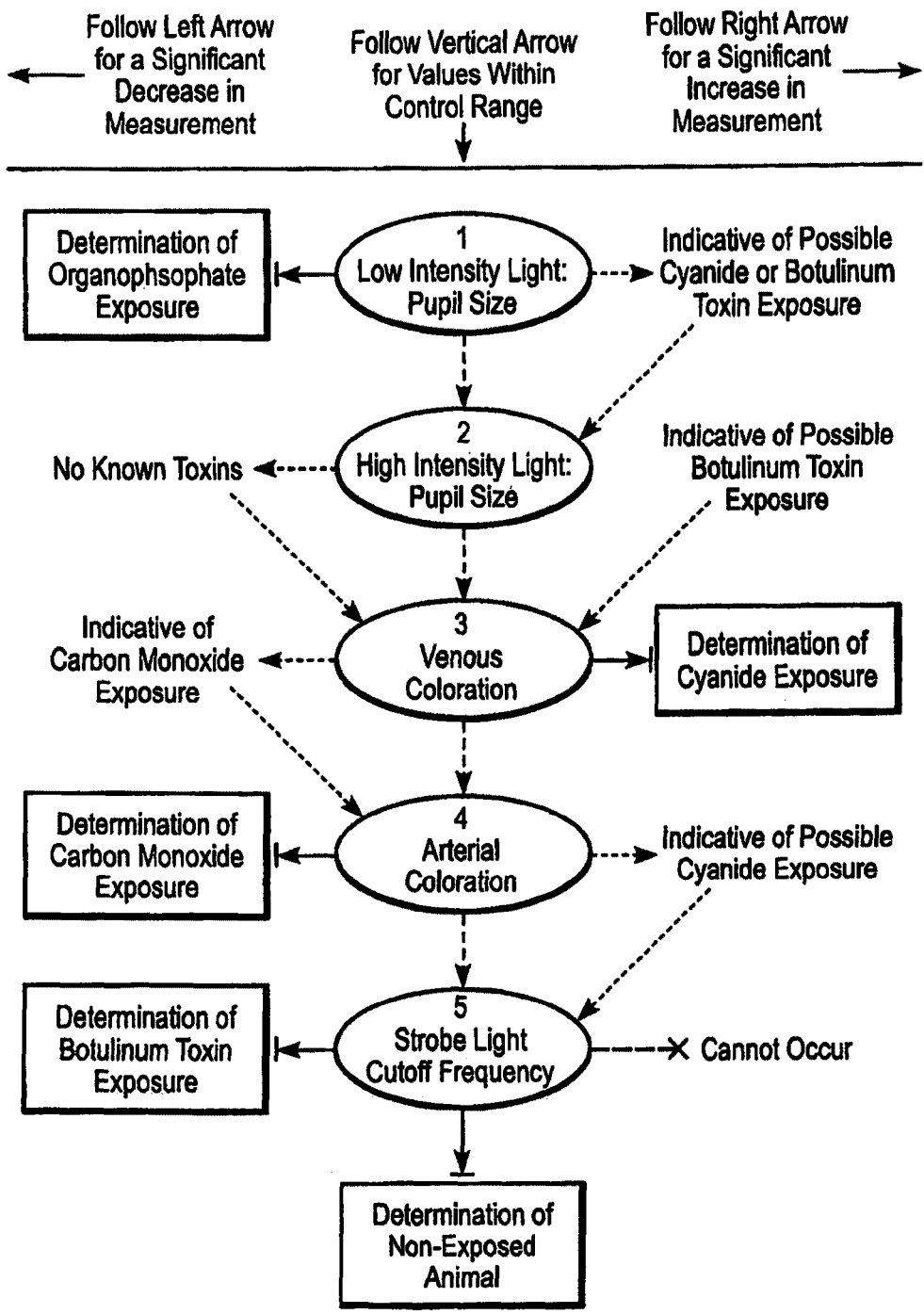
FIG. 1 is a flow chart showing an exemplary embodiment of a method for diagnosing exposure to a biological agent or chemical toxin.
Figure 2:
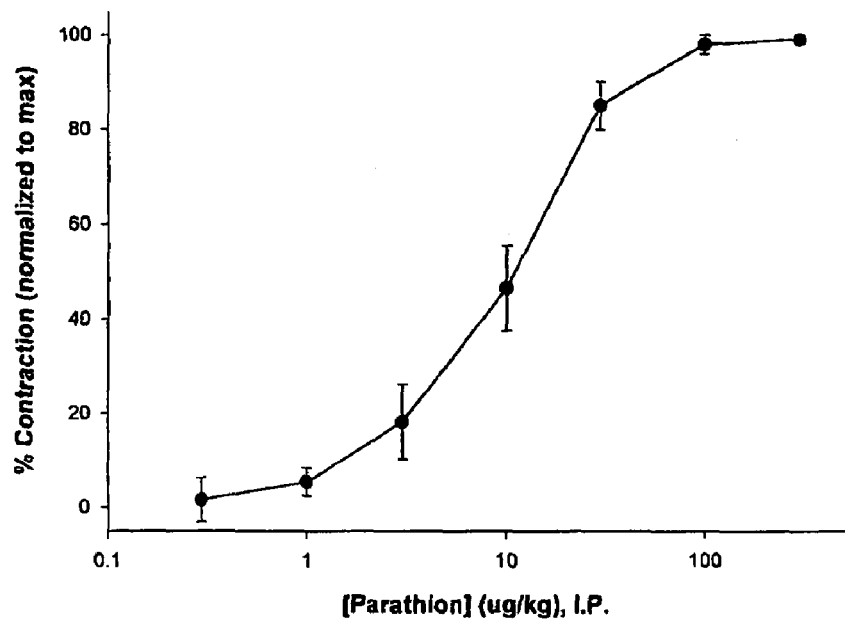
FIG. 2 is a concentration-response curve for Sprague-Dawley rats 5 minutes after direct ocular exposure to parathion.

An ocular characteristic is a measurable physical attribute determined via the observation of external and/or internal features of the eye(s). Non-limiting examples of ocular characteristics include pupil size, pupillary light reflex, pupil motility, strobe light frequency cutoff, blood vessel coloration, blood vessel architecture, ischemic spots, exudate appearance, and cellular degeneration. An altered ocular characteristic can be the result of a disease state. In many instances, an altered ocular characteristic is specific for a particular disease state. This need not be the case, however, for the method of the present invention to be useful, as it is the cumulative evaluation of multiple ocular characteristics which often results in a specific diagnosis. In addition, particular diseases often can be eliminated from a differential diagnosis based upon the subject's medical history. For example, while a soldier deployed in combat and a worker in a paint factory may both exhibit the same altered ocular characteristics, a different diagnosis can be reached based upon the risk factors associated with the respective environments to which each is exposed.

Disease State

The term "disease state," optionally referred to simply as "disease," is intended to encompass not only the meaning as commonly understood by those skilled in the art to which this invention belongs but also conditions not necessarily pathological in nature. For purposes of this invention, a disease state is any condition the existence of which results in an alteration to one or more ocular characteristics in the subject. Non-limiting examples of a disease state include biological toxin or chemical agent exposure, systemic hypertension, internal trauma, inadequate nutritional status, and altered cognitive state. Biological toxins and chemical agents include, but are not limited to: organophosphates, cyanide, carbon monoxide, and *botulinum* toxin.

Organophosphates

Many organophosphates (OPs), including tabun, sarin, soman, syclosarin, and VX, are nerve agents that can be used for chemical warfare. Other members of the OP group are commonly used as agricultural pesticides (e.g., Malathion, Parathion, Trichlorfon, etc.). The OPs share a similar chemical structure and are derivatives of phosphoric or phosphonic acids containing two alkyl groups and a leaving group. The primary pharmacological effect of the OPs is to inhibit the enzyme acetylcholinesterase (AChE) via phosphorylation of a serine hydroxyl group in the active site of the enzyme. AChE normally functions to quickly destroy acetylcholine (ACh) in the synaptic cleft and thus terminate transmission of a nerve impulse. Inactivation of AChE results in the accumulation of ACh, which causes an initial enhancement and prolongation of cholinergic activity followed by depolarization blockade.

Cyanide

The cyanides, when compared to other lethal chemical warfare agents, are the least toxic. However, though these agents may be less potent in their lethality, they act very quickly and thus diagnosis and subsequent actions to combat their effects must commence promptly after exposure. The cyanides of military interest are the volatile liquids: hydrogen cyanide (HCN), cyanogen chloride (ClCN), and cyanogen bromide (BrCN). The pharmacological and toxicological effects of the cyanides (due to cyanide [CN⁻]) are identical, but the cyanogens are additionally irritant to the eyes and respiratory tract. Cyanide acts by combining with the ferric ion in mitochondrial cytochrome oxidase, preventing electron transport in the cytochrome system and, thus, bringing oxidative phosphorylation and ATP production to a halt. Though fully oxygenated, the cells cannot utilize the oxygen and thus increased demands are placed on anaerobic glycolysis. This results in lactic acid production/accumulation and eventual cell death due to histotoxic anoxia.

Carbon Monoxide

Carbon monoxide (CO) is a colorless, odorless gas which comes from numerous sources. Part of CO's acute toxicity results from the fact that it essentially replaces the oxygen in the blood. Hemoglobin (Hgb), the oxygen carrying molecule of the blood, has an affinity for CO which is approximately 200-250 times greater than that for oxygen. The absorption of CO by the blood (creating carboxyhemoglobin) causes a leftward shift in the oxygen-hemoglobin dissociation curve, resulting in a decreased oxygen carrying capacity and impaired release of oxygen to the tissues. This, in turn, leads to cellular/tissue hypoxia. The relatively high affinity of Hgb for CO also results in a relatively persistent effect in individuals well after they've been removed from exposure to the gas.

Though. carbon monoxide poisoning generally results from chronic exposure to lower levels of CO, there are many documented cases of acute poisoning. In addition, the relatively low level of toxicity and reversibility of CO poisoning has allowed more extensive human studies to be performed than with many other toxins. The brain and heart, by virtue of their high metabolic activity, appear to be the most rapidly affected sites of CO poisoning. Unfortunately, many of the early warning signs for CO poisoning are similar to common flu-like symptoms: headache, nausea, dizziness, etc. In cases of more severe poisoning, the clinical findings may be very similar to that of cyanosis (cyanide poisoning; see above). This is somewhat to be expected in that both carbon monoxide and cyanide deprive tissues/cells of the ability to utilize oxygen. However, the different pathways by which these toxins reach this physiological endpoint may be of use in the quick determination of the type of poison in the system. As described above, for cyanide poisoning the hemoglobin/blood is fully oxygenated but the cells are deprived the ability to utilize this oxygen. On the other hand, with CO poisoning the hemoglobin/blood is severely under-oxygenated due to the formation of carboxyhemoglobin. This altered level of blood oxygenation is discernable based upon the coloration of the blood which is primarily determined by hemoglobin and its level of oxygenation.

Hemoglobin (Hgb), the red blood pigment, provides the oxygen-carrying capacity of the blood. The high concentration (34 gm/dL) of Hgb within erythrocytes (red blood cells) allows oxygen ($O_2$) to be circulated at concentrations as high as 0.01 M, which is approximately the same as atmospheric air. This oxygen concentrating ability is accomplished via a number of factors. Hgb is composed of four subunits, each of which noncovalently binds a single heme group. The heme molecule, which is responsible for the characteristic red color of blood, is the site at which each Hgb subunit binds one molecule of $O_2$. Thus, each Hgb molecule may bind four molecules of $O_2$ (one per subunit). Furthermore, this oxygen is bound cooperatively. That is, when the Hgb binds a molecule of $O_2$, its affinity for binding another molecule of $O_2$ is increased. Thus, the fourth $O_2$ molecule to bind Hgb does so with 100-fold greater affinity than did the first. The reverse is also true. As oxygen begins to unbind upon reaching the tissues, the affinity for the still-bound $O_2$ decreases such that each successive molecule more easily dissociates. This simple property of Hgb provides the foundation for highly efficient loading of oxygen in the lungs and unloading in the tissues. In addition to its role as an $O_2$ carrier, Hgb also plays an important role in the transport of $CO_2$, acquiring it in the tissues and subsequently releasing it in the lungs for expiration.

Botulinum Toxin

Botulinum toxin is the most poisonous substance known to man with a single gram of the crystalline toxin possessing the ability to kill more than 1 million people. Because of this extreme potency and lethality, as well as its ease of production and transport, botulinum toxin poses a major bioweapons threat. Botulinum toxin is a protein neurotoxin produced by various subtypes of the bacterium Clostridium botulinum, an anaerobic, gram-positive organism. Unable to penetrate intact skin, botulinum toxin requires a wound, ingestion, or inhalation to exert its effects. Upon gaining access to the general circulation, botulinum toxin binds with extremely high affinity to peripheral cholinergic nerve endings at the neuromuscular junction and in the autonomic nervous system (preganglionic sympathetic and parasympathetic, postganglionic parasympathetic nerve terminals). Once in the target cell, the toxin acts as a zinc-dependent endoprotease, cleaving polypeptides that are essential for the exocytosis (release) of acetylcholine (ACh). Botulinum toxin is both highly selective for cholinergic neurons and long lasting—clinically significant responses may last from several months to a year.

The human data concerning botulinum toxin effects comes primarily from cases of food-borne (ingested) and wound exposure. The classic clinical features of botulism (the disease caused by botulinum toxin exposure) are symmetric cranial neuropathies (i.e., ptosis [drooping eyelids], weakened jaw clench, dysarthria [speech disturbances], and dysphagia [difficulty swallowing]), diplopia (double-vision) or blurred vision, peripheral muscle weakness, respiratory dysfunction, and gastrointestinal distress (nausea and vomiting). In addition, pupillary light reflexes are typically depressed or absent and the pupils are dilated (mydriasis). With time, peripheral muscle weakness will progress to flaccid muscular paralysis and death results from respiratory muscle paralysis. Though little is published regarding the bioterrorist or military use of botulinum toxin, it is believed that such an attack (food-borne or aerosolized) would yield similar symptoms presenting 12-72 hours after exposure. In the case of inhalational exposure, the clinical presentation would be identical but the gastrointestinal symptoms would likely be absent.

Method of Diagnosing a Disease State

The present invention includes a method of diagnosing a disease state in a subject. The subject can be any member of the animal kingdom, such as dogs, monkeys, rats, etc., but preferably is a human being (person). The method of diagnosing the disease state preferably includes the steps of 1) examining the subject's eyes in order to determine whether the subject exhibits an ocular characteristic indicative of the disease state, and if so; 2) evaluating the ocular characteristic in order to diagnose the disease state, including its severity. One or more altered ocular characteristics can indicate the existence of a disease state in a subject.

In a presently preferred embodiment, a subject's eyes are examined passively rather than actively. A passive examination is distinguished from an active examination based upon the degree of participation by the subject. During a passive examination, the examiner may manipulate the eyes with lighting, etc., but the subject is not required to voluntarily act or react to external stimuli. In contrast, the subject does participate during a typical active examination, for example by tracking with his or her eyes a light or the examiner's finger. The subject's eyes preferably are examined by evaluating one or more ocular characteristics. For example, it may be desirable to examine a subject's eyes by sequentially evaluating pupil size, pupillary light reflex, ocular blood vessel coloration, and strobe light cutoff frequency. By sequentially analyzing a variety of ocular characteristics, a diagnosis can be made either manually by a caregiver, or automatically, i.e., without the need for manual measurement, analysis, or diagnosis, by a processing unit or other similar means employing a decision tree or an algorithm.

In a presently preferred embodiment, ocular characteristics of a subject's eye are evaluated by first quantifiying the ocular characteristic under consideration. For example, the diameter of the subject's pupil can be measured and assigned a numerical character corresponding to the diameter. This number, or quantity, can then be compared easily to a normal pupil under similar conditions, which also has been quantified by assigning an appropriate numerical character. The norm for the ocular characteristic, in the case of this example the normal pupil size, preferably is established for each subject being examined. However, average normal values also can be established for different populations and sub-populations. A subject's quantified ocular characteristic data can then either be compared to his or her personal normal value, or it can be compared to an average normal value established for a population to which the subject belongs. In so doing, a person examining a subject's eye can determine whether one or more ocular characteristics have been altered.

Pupil Size

Referring generally to FIG. 1, pupil size preferably is one of the ocular characteristics evaluated when examining the subject's eyes. The pupil(s) preferably are evaluated to assess whether there has been a significant increase (dilation) or decrease (miosis) in the diameter of the pupil(s). Non-limiting examples of times at which it may be desirable to analyze a subject's pupil size are after suspected or possible exposure to a biological toxin or chemical agent, when the subject displays symptoms of or is at risk for developing systemic hypertension, when there is a possibility that the subject has suffered a blunt head injury, as part of a routine check-up or health screening, and after the occurrence of any other event likely to induce a disease state in the subject.

In order to determine whether there has been a significant change in pupil size, a baseline, or "normal," pupil size preferably is established. A normal pupil size preferably is established for each subject by measuring the diameter of each subject's pupil(s) under a controlled setting, i.e., controlled lighting, etc. Alternatively, an average (or baseline) pupil size for a given population to which the subject belongs can be used as the normal pupil size for all members of the population. While examining a subject's eye, the diameter of the subject's pupil preferably is measured. The subject's pupil(s) preferably are evaluated in two settings—one with low intensity light (for example about 1.7 $cd/m^2$), and the second with high intensity light (for example about 80 $cd/m^2$). As shown in FIG. 1, a significant decrease in pupil size (pupil contraction or "miosis") in low intensity light can indicate organophosphate exposure.

The extent of organophosphate exposure can be evaluated by examining whether the subject's pupil(s) retain their ability to contract and dilate in response to altering light conditions (pupillary light reflex). Pupil(s) retain their pupillary light reflex when subjects are exposed to relatively low levels of an organophosphate. The pupillary light reflex is eliminated, however, when subjects are exposed to relatively high levels of an organophosphate. After organophosphate exposure is diagnosed, the extent of the exposure can be determined by repeatedly exposing the affected subject's pupil(s) to a high intensity light followed by a low intensity light. Those subjects in which the pupillary light reflex has been eliminated (or greatly reduced) have been exposed to relatively high levels of an organophosphate. In contrast, those subjects in which the pupillary light reflex remains intact have been exposed to relatively low levels of an organophosphate. This aspect of the invention can be especially useful as a means for triaging casualties in military field operations where masses of military personnel can possibly be exposed to chemical warfare agents at the same time. As shown in FIG. 1, a significant increase in pupil size (dilation) in low intensity light can indicate possible cyanide or *botulinum* toxin exposure. Pupil dilation in high intensity light is a further indicator of possible *botulinum* toxin exposure.

A subject's pupil(s) can be examined using various means commercially available and known to those skilled in the art. In a presently preferred embodiment, the subjects' pupil(s) are examined using infrared and visible frequency adjustable lighting and adequate resolution black and white infrared and color near-infrared CCD (charge-coupled device) and color visible wavelength cameras.

Ocular Blood Vessel Coloration

Ocular blood vessel coloration preferably is another ocular characteristic evaluated when examining a subject's eye. Ocular blood vessel coloration preferably is examined to assess whether there has been a significant change, e.g., increased brightness or darkness, of the blood in the ocular blood vessels. Non-limiting examples of times at which it may be desirable to analyze a subject's pupil size are after suspected or possible exposure to a biological toxin or chemical agent, when the subject displays symptoms of or is at risk for developing systemic hypertension, when there is a possibility that the subject has suffered a blunt head injury, as part of a routine check-up or health screening, and after the occurrence of any other event likely to induce a disease state in the subject. Ocular blood vessels include, but are not limited to: arteries, veins, venules, capillaries, and arterioles.

In order to determine whether there has been a significant change in ocular blood vessel coloration, a baseline, or "normal," color preferably is first established for certain ocular blood vessels, e.g., retinal veins and arteries. Normal coloration preferably is established for each subject using a modified fundoscope for imaging the internal regions of the eye under non-mydriatic conditions. Alternatively, an average (or baseline) ocular blood vessel coloration for a given population to which the subject belongs can be used as the normal vessel coloration for all members of the population. While examining the subject's eye, fundoscopic images of the internal regions of the subject's eyes can be obtained for comparison purposes. As shown in FIG. 1, a significant increase in the brightness of the retinal veins can indicate possible cyanide exposure. Significantly increased brightness of the retinal veins, combined with an increase in pupil size in low intensity light, can lead to a definitive diagnosis of cyanide exposure. In contrast, a significant decrease in brightness of the retinal veins can indicate possible carbon monoxide exposure. A diagnosis of carbon monoxide exposure can be confirmed by analyzing retinal artery coloration. A significant decrease in brightness of the retinal arteries, combined with a significant decrease in retinal vein brightness, can lead to a definitive diagnosis of carbon monoxide exposure.

Arterial coloration also can be useful as a secondary characteristic for assessing the severity of cyanide exposure. Whereas retinal vein coloration is affected at relatively low doses of cyanide exposure, retinal artery coloration is not affected until the subject has been exposed to relatively high doses of cyanide. This differential sensitivity of the retinal veins and arteries is a useful method for determining the severity of cyanide exposure. A similar phenomenon exists with carbon monoxide exposure. Whereas retinal artery coloration is affected at relatively low doses of carbon monoxide exposure, retinal vein coloration is not affected until the subject has been exposed to relatively high doses of carbon monoxide: An analysis of the differential response of retinal arteries and veins thus also can be useful for determining the severity of carbon monoxide exposure.

Ocular blood vessels, including retinal arteries and veins, can be examined using various means known to those skilled in the art, such as a fundoscope. The fundoscope preferably can be converted to a digital video fundoscope by making modifications such as: altering shutter mechanics, adapting the mounting means to allow a CCD camera to be attached, and refocusing/magnifying the light source and image capture means to provide fundoscopic images with increased clarity. Alternatively, a commercially available digital fundoscope could be used.

Strobe Cutoff Frequency

Strobe light cutoff frequency preferably is another ocular characteristic evaluated when examining a subject's eye. In normal, i.e., healthy or disease-state-free, subjects, there is a maximal frequency at which the pupillary light reflex can function. This frequency is limited by the frequency at which impulses denoting a light flash can travel from the retina, through the pupillary light reflex loop, and back to the muscles controlling pupil size for effect. For comparison purposes, this value is considered the normal (or baseline) strobe light cutoff frequency. The normal strobe cutoff frequency preferably is determined empirically for each subject. Alternatively, an average (or baseline) cutoff frequency for a population to which the subject belongs can be determined and used.

At a pre-determined time, strobe cutoff frequency is obtained for comparison purposes. A significant decrease in the maximal response frequency after over-stimulation with high intensity light flashes can indicate *botulinum* toxin exposure. Strobe cutoff frequency preferably is examined using a tunable strobe device for applying various intensities of light at known frequencies.

EXAMPLES

The following examples are from studies employing a rodent model (Sprague-Dawley rat) of exposure.

Example 1

Intraperitoneal Exposure to Organophosphates

Parathion is an organophosphate insecticide which has an identical mechanism of action to that of the organophosphate nerve agents (e.g., Soman, Sarin, VX, etc.) but has decreased potency compared to the warfare agents. Parathion was diluted in corn oil as necessary for dosing. The literature $LD_{50}$ values (dose required to kill 50% of those animals exposed) were first validated for parathion. The literature value for rats exposed to intraperitoneal (I.P.) parathion is 2 mg/kg (i.e., 2 mg parathion per kg of rat body weight). The findings in the present study were consistent with this value—extrapolated $LD_{50}$ value from concentration-response (death) curves was 2.47±0.67 mg/kg (±standard deviation). The lowest dose found to be lethal in any animal tested within 48 hours of administration (standard time length for $LD_{50}$ testing) was 1.00 mg/kg. This occurred for only 1 of 5 animals tested at this dose.

Upon validation of the literature $LD_{50}$, a concentration-response curve for miosis (pupillary contraction) at various times post-exposure was constructed. Animals were weighed and then briefly anesthetized with the inhalational anesthetic halothane (Sigma-Aldrich, St. Louis, Mo.) and given an I.P. injection of parathion (Supelco, Bellefonte, Pa.). The parathion stock concentration was chosen for each group of animals such that the total volume administered to each animal was from 0.2 to 1.0 ml. The data discussed below is in relation to individual controls (i.e., control pupil diameter values were obtained for each animal prior to injection of parathion). For proper control purposes, however, a group of animals (n=7) was given 1 ml corn oil I.P. to ensure lack of miotic effect of the vehicle (percent change in pupil size 60 minutes after injection=0.28±0.97%).

Test animal pupils were monitored and recorded continually post-injection of parathion for a period of 60 minutes under very low light intensity conditions (1.7 cd/$m^2$) using CCD cameras (color and infrared). At specific time points during these recordings (5, 10, 15, 30, and 60 minutes), the animals were subjected to "steps" in light intensity for pupillary light response analysis. For each time point indicated, this involved 1 minute of high intensity lighting (80 cd/$m^2$) followed by return to baseline low level lighting intensity. Though the restricted time analysis may not allow for full dark/light adaptation, it did supply sufficient responses for temporal analysis of early pupillary light reflexes around each time point investigated and provided more opportunities to examine light reactivity than would the analysis of full adaptive responses. The concentration-response curve (for miosis/percent pupillary contraction) 15 minutes post-parathion injection is illustrated in FIG. 2, in which all values have been normalized to the maximal pupillary contraction observed among all parathion exposed animals (93.1%; 3 μg/kg), light intensity=1.7 cd/$m^2$, error bars represent ±S.E.M, and extrapolated $EC_{50}$ is 147±36 ng/kg.

The pupillary light reflex was also analyzed in these animals. Though this reflex (contraction of pupil in response to increased light intensity and dilation of the pupil in response to decreased light intensity) was altered and sometimes absent in animals at lower doses of parathion, it was not completely absent for all animals until the dosing reached a level of 30 mg/kg ($EC_{50}$ for loss of pupillary light reflex=953±69 μg/kg). This differential potency of organophosphates for miosis and abolition of the light reflex thus can serve as a beneficial diagnostic tool.

Miosis is a relatively sensitive ocular characteristic for organophosphate exposure with a diagnostic index (ratio of miosis $EC_{50}$ to compound $LD_{50}$) of approximately 200 (e.g., occurs at doses 200-fold less than those found to be lethal) in the case of I.P. injection and approximately 14,000-fold for direct ocular exposure. In addition, the fact that loss of the pupillary light reflex occurred at slightly greater levels of organophosphate intoxication than did miosis, provides an additional diagnostic tool for use during ocular examination. That is, not only may ocular analysis serve to diagnose whether an animal/individual has been exposed, but it may also provide information as to the level of exposure. Such differential diagnosis with regard to the severity of exposure may prove extremely useful in possible triage cases where large numbers of individuals have been exposed to various levels of agent and categorizing individuals with respect to medical need is vital.

Example 2

Direct Ocular Exposure to an Organophosphate

In addition to the intraperitoneal studies described above, groups of animals were also exposed to direct ocular parathion to better simulate likely warfare exposure (vapor exposure to the eyes and respiratory tract). These studies were conducted identically to those described above except that rather than I.P. injection, the left eye was exposed to 0.05 ml of the parathion concentration for a period of 3 minutes and then washed with saline. During the application period, animals were held under light (1%) halothane anesthesia to prevent unwanted movements or blinking which might alter the application time/integrity. Times post-exposure represent the amount of time elapsed from initial parathion application (i.e., parathion was washed off at 3 minutes post-exposure).

Figure 3:
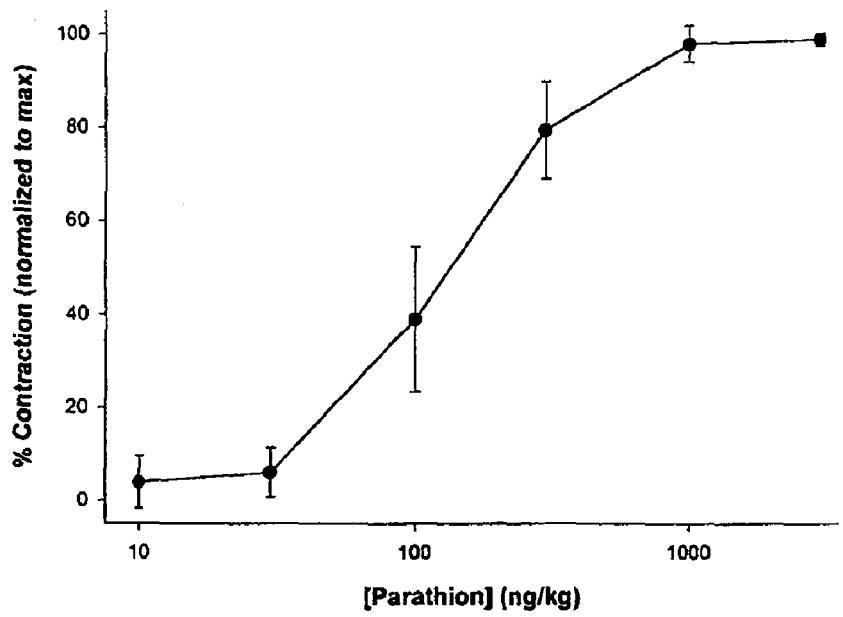
FIG. 3 is a concentration-response curve for Sprague-Dawley rats 5 minutes after direct ocular exposure to parathion.

FIG. 3 shows the concentration-response curve for 5 minutes post-direct ocular exposure. The earlier time point was chosen for these studies as miosis developed much more rapidly via exposure by this route. Similar to the findings for I.P. parathion, the loss of the pupillary light reflex occurred at slightly higher concentrations than did miosis. The first group of animals in which all lacked such a response was the 10 µg/kg group with an $EC_{50}$ for loss of the light reflex equal to 2.8±0.9 µg/kg. In FIG. 3, all values have been normalized to the maximal pupillary contraction observed among all parathion exposed animals (93.1%; 3 µg/kg). Light intensity=1.7 cd/m$^2$. Error bars represent ±S.E.M. Extrapolated $EC_{50}$ is 147±36 ng/kg.

Example 3

Exposure to Cyanide

The $LD_{50}$ for potassium cyanide (KCN; Sigma-Aldrich, St. Louis, Mo.) was validated. using subcutaneous KCN. The experimental $LD_{50}$ value for subcutaneous KCN was 6.7±0.6 mg/kg compared to literature values ranging from 6 to 9 mg/kg. Studies were done with both anesthetized (with Ketamine/Xylazine, Sigma-Aldrich, St. Louis, Mo.) and unanesthetized animals. No differential effects were observed. Animals that survived the first two hours after KCN exposure, survived for the duration of the two day (48 hour) observation, demonstrating the highly acute effects of cyanide overexposure.

For completion of the studies, a rat model (Sprague-Dawley) of subcutaneous (S.C.) exposure to KCN was employed. For all experiments, KCN was dissolved in normal saline such that a volume between 0.2 and 1.0 ml would be injected. As with the parathion experiments, post-injection data was compared to control data obtained prior to injection of KCN for each animal. In addition, a group of animals was given 1.0 ml saline S.C. as an added control group. These studies were performed with a modified fundoscope for imaging the internal regions of the rat eye under non-mydriatic conditions. Due to the requirement of having the animals remain very still during recording, long term anesthesia with a ketamine/xylazine mixture (80 mg/kg ketamine hydrochloride; 12 mg/kg xylazine hydrochloride) was induced prior to recording.

Figure 4:
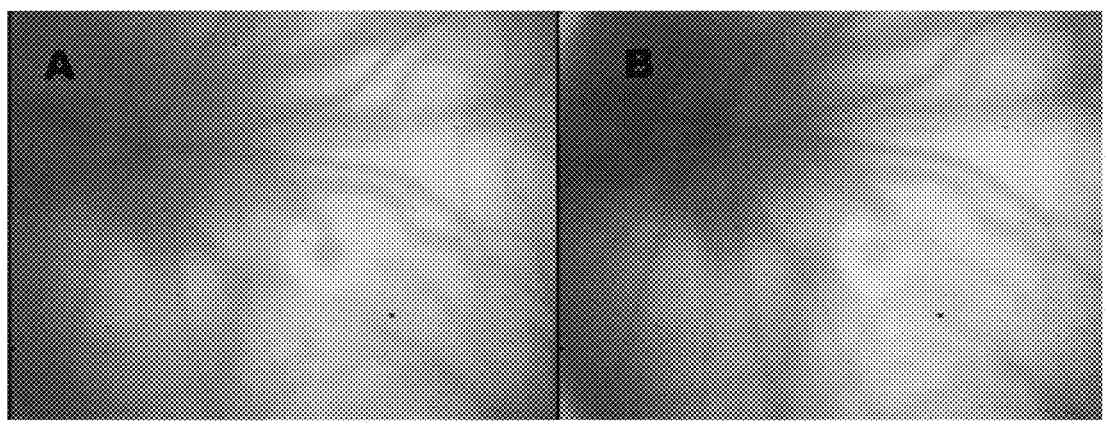
FIG. 4 is a fundoscopic image of a Sprague-Dawley rat eye (A) prior to, and (B) 2 minutes after subcutaneous injection 10 mg/kg KCN (faded circular object in the center of each image is a reflection of the light source from the fundoscope).

The experimental procedure was as follows: animals were weighed, anesthetized with ketamine/xylazine, and then placed on an adjustable platform in position for proper fundoscopic imaging. Approximately 10-15 minutes after anesthetic induction, a needle (23-gauge) attached to a 1 ml syringe containing KCN was inserted under the skin and between the rear shoulder blades of the animal. Baseline fundoscopic imaging was then continually recorded. Five minutes after the beginning of recording, the plunger on the 1ml syringe was depressed, subcutaneously injecting the animal with KCN. Images were continually recorded for 60 minutes or until death (whichever came first). Example images from one of the animals are shown in FIG. 4.

Subsequent to obtaining streaming images, individual images from the streaming video were isolated at specific time periods. Vessel coloration was then quantitatively analyzed. Arteries and veins were identified and subsequently isolated based on characteristic presentation (caliber, location, etc.). When possible, A-V pairs (adjacent artery and vein) were evaluated to minimize any illumination-induced measurement errors. In order to complete the analysis, a number of different digital signal processing (DSP) methods were examined and tested for optimizing the discrimination capabilities of the system while accounting for the expected variability between individuals (in this case animals). Initial analysis was conducted using very simplistic processing algorithms. This involved simply converting the images to a gray scale, determining the average coloration of the vessel of interest (0-255), and then using these values to determine the means and standard errors for subsequent analysis. Via these preliminary analytical methods, the lowest level of subcutaneous KCN that was found to yield statistically significant differences was 1.0 mg/kg.

In an attempt to increase the discriminatory capabilities of the vasculature analysis protocol, additional signal processing techniques were implemented and evaluated. Working with gray scale images greatly enhanced the efficiency of analysis and interpretation of effects. In addition, statistical comparison of the linear output values of the gray scale was more convenient for the current goal of establishing venous blood coloration as a characteristic for cyanide exposure. Though use of the full color range to analyze images provides greater sensitivity (16.8 million colors vs. 256 gray scale colors), such analysis also requires a much more complex three-dimensional (RGB; red-green-blue) comparison.

Incorporating color images with automated algorithmic analysis could provide a much more powerful discriminatory ability, but is not required for the present purposes. For that reason, a relatively non-cumbersome route for the manual analysis was used. The process involved (1) converting the color images to gray-scale (0-255), (2) flattening the illumination characteristics, and (3) using histogram equalization to improve contrast in the color range which the vessels reside. All of these functions were performed using the commercially available product, Corel® Draw™ 11 (Corel Corporation, Ottawa, Ontario, Canada). Once conversion was completed, the original image, processed image, and analytical values were archived. Employing these basic processing techniques allowed for relatively rapid analysis times while significantly enhancing the sensitivity of the measurements for cyanide exposure diagnosis. This improved sensitivity was evidenced by decreasing the KCN dose which yielded statistically significant observable differences from 1.0 mg/kg (as above) to 30 µg/kg (see below), a 30-fold enhancement of diagnostic capabilities.

Figure 5:
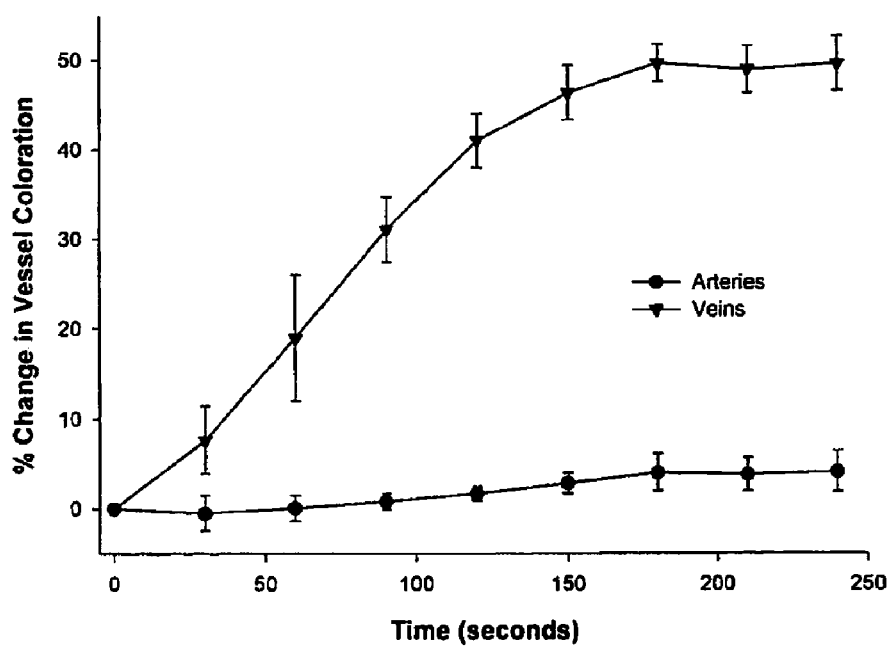
FIG. 5 shows the percent change in arterial and venous vessel coloration in Sprague-Dawley rats in response to subcutaneous injection of 1 mg/kg KCN over time, n=6. Percent changes are compared to pre-dosing individual control levels. Change in venous coloration became statistically significant (p<0.05) at the 90 second time interval. Means have been normalized to initial control values and error bars represent ±S.E.M.

After exposure to KCN, the onset of altered blood coloration, generalized exposure signs/symptoms, and death (after large lethal doses) is quite rapid, even with the subcutaneous route of application. As seen in FIG. 5, in response to 1 mg/kg KCN (s.c.), arterial vessel coloration did not change significantly (though there was a slight trend toward brighter coloration) whereas venous coloration brightened significantly within 60 seconds of cyanide injection (p<0.05).

Figure 6:
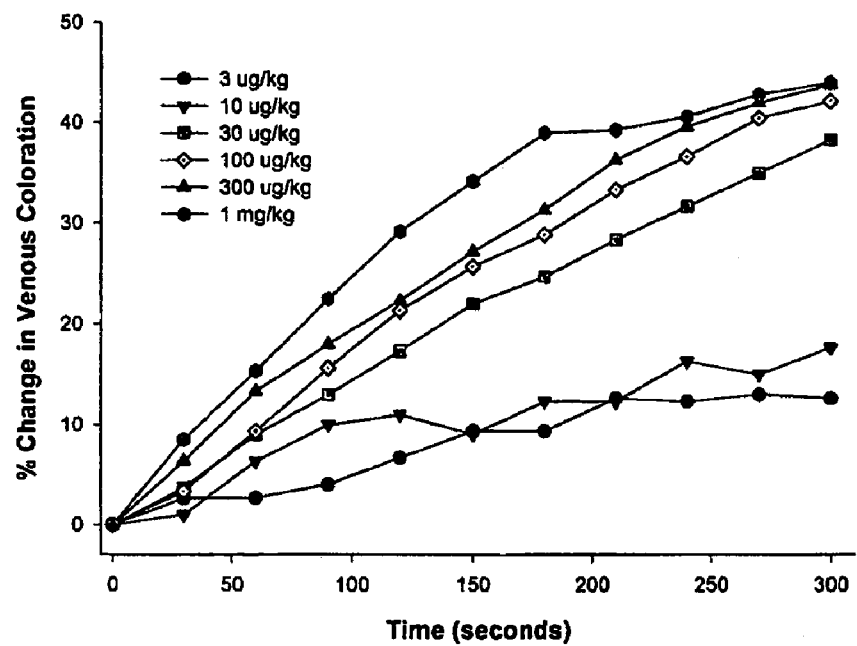
FIG. 6 shows the percent change in venous vessel coloration in representative Sprague-Dawley rats in response to subcutaneous injection of various concentrations of KCN over time. Percent changes are compared to pre-dosing individual control levels (normalized to control). Error bars have been omitted for clarity.

These alterations in venous coloration/oxygenation were often quickly followed by generalized symptoms such as rapid respiration with increased depth of breath. Maximal changes in venous coloration were typically noted within five minutes of KCN administration. FIG. 6 plots the time course of venous coloration change in response to various concentrations of I.P. KCN.

Figure 7:
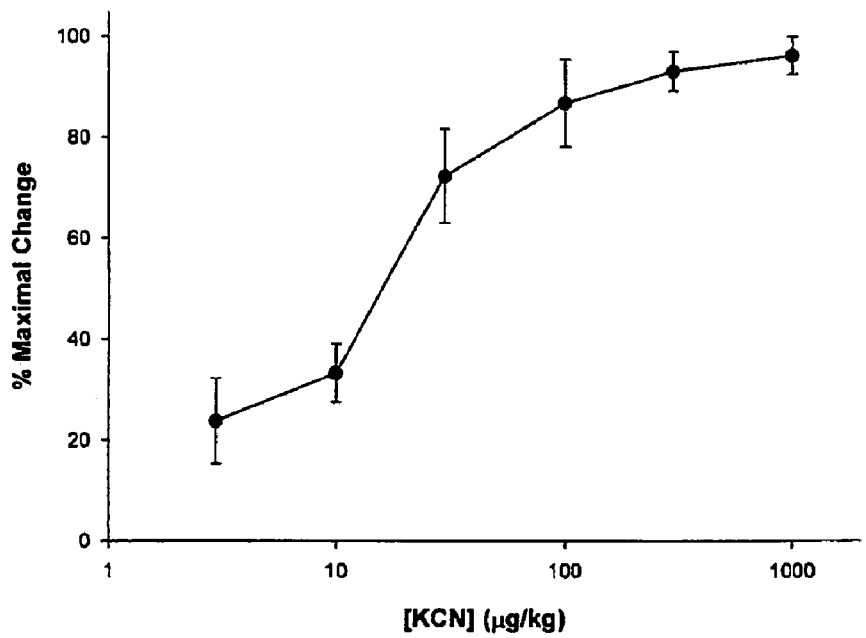
FIG. 7 shows a concentration-response curve for venous coloration changes in Sprague-Dawley rats in response to subcutaneous injection of KCN. Data was obtained 5 minutes after KCN injection. Extrapolated $EC_{50}$ =24.6±3.1 µg/kg. Percent changes are compared to pre-dosing individual control levels. Means have been normalized to the maximal observed change in all animals (53%) and error bars represent ±S.E.M.
Figure 8:
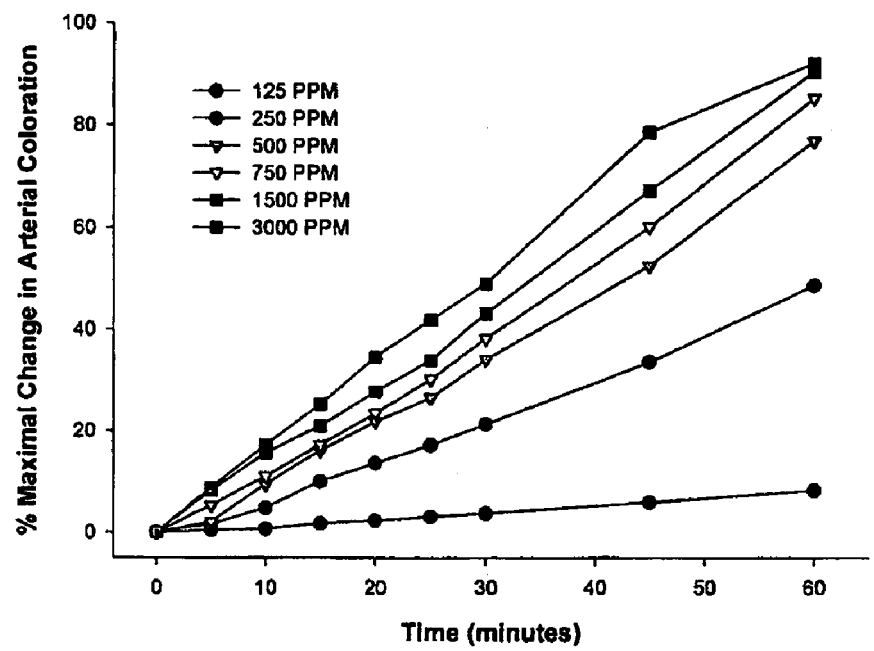
FIG. 8 shows the percent change in arterial vessel coloration (normalized to control) in representative Sprague-Dawley rats in response to inhalational application various levels of carbon monoxide over time. Error bars have been omitted for clarity.

For construction of the concentration-response relationship between KCN and venous coloration, the 5 minute post-administration time point was chosen for analysis. As noted above, all changes in venous coloration reached a maximum level by this time point and only animals which were administered supramaximal lethal doses of 30 mg/kg or greater expired within this time frame. Curve fitting analysis of the concentration-response curve shown in FIG. 7 for venous coloration change 5 minutes after subcutaneous KCN injection estimated an $EC_{50}$ for maximal detected venous color change of 24.6±3.1 μg/kg. However, statistically significant changes were not seen in every animal examined until the 30 μg/kg test group (p<0.05).

In addition to the approximate 200-fold diagnostic window ($LD_{50}$=6.7 mg/kg; significant venous changes at 30 μg/kg) provided by venous alterations, it also became apparent that there may be some diagnostic utility in the analysis of arterial coloration. We found a slight but significant increase in the color value of the arteries at greater KCN dosage levels. This change became significant at the 300 μg/kg level (p<0.05). Since the arterial coloration does not appear to be as sensitive a diagnostic indicator for KCN exposure it may be useful as a secondary indicator for exposure level, much as the pupillary light reflex appears to be useful for organophosphate exposure. Thus, an indication of significant coloration changes (to brighter, more oxygenated levels) in both arterial and venous systems indicates a greater level of exposure than venous changes alone. Furthermore, it should be noted that only animals which displayed changes in both systems (arteries and veins) later died as a result of their exposure. Thus, in mass casualty situations this may provide a valuable discriminating tool to identify individuals who have been exposed to sublethal levels of cyanide versus those who have been exposed to potentially lethal levels of the compound. With more advanced signal processing methods, this discriminatory capability may be further increased.

Example 4

Exposure to Carbon Monoxide

As was done for each of the agents previously discussed, an initial analysis of the lethal effects of CO was performed. The nature of CO, namely that it is a gas, places such experiments more at the discretion of the researcher. Whereas with chemicals/toxins a standard single injection $LD_{50}$ study may be employed, with inhalational agents there is the added variable of application time. A 48-hour administration of CO is not feasible (would require continual animal monitoring) and there is no standard protocol for such tests. Thus, reported values for lethal levels of various gases/gas mixtures vary with respect to both concentration of gas and length of application. Often these reported values will be for lethal effects ensuing after 4 or 8 hours of gas administration. However, since the protocol used for the studies described here employ a 60 minute observation window, the 1 hour time point was used for the lethality determination endpoint. The 60 minute exposure $LD_{50}$ determined in the present studies was 3123±476 ppm (parts-per-million).

In addition to changes in lethality testing analysis, the route of exposure (inhalation) mandates changes to the dosing protocol. Typically, as evidenced in dosing patterns plotted in figures for previous agents, single injection agents are dosed based on the normal logarithmic concentration-response characteristics. Thus a dosing pattern of 1, 3, 10, 30, etc. is normally employed to give a symmetrical log-dose comparison. However, the compounding effect of continual gas exposure leads to a toxic load which makes such dosing patterns impractical for proper quantitative analysis, as they will not yield concentration-response curves which sensitively and accurately reflect the actions of the gas (i.e., the dose ranges are too broad/diffuse). For this reason, variable increments in carbon monoxide percentage were used in the present experiments, concentrating primarily around the region of initially observable significant effects.

For completion of the studies, a rat model (Sprague-Dawley) of inhalational exposure to CO was used. As with the previous experiments, post-exposure data was compared to control data which was obtained prior to CO administration for each animal. In addition, a group of animals was connected to the inhalational exposure apparatus and administered compressed normal air (79% nitrogen, 21% oxygen) as an added control group. Imaging studies were performed with a modified fundoscope for imaging the internal regions of the rat eye under non-mydriatic conditions. Due to the requirement of having the animals remain very still during recording, long term anesthesia with a ketamine/xylazine mixture (80 mg/kg ketamine hydrochloride; 12 mg/kg xylazine hydrochloride) was induced prior to recording.

Experimental procedures were as follows: animals were weighed, anesthetized with ketamine/xylazine, and then placed on an adjustable platform in position for proper fundoscopic imaging. The animals were then connected to the inhalation apparatus and allowed to breathe normal air. Approximately 10 minutes after initial anesthetic induction, baseline fundoscopic images were continually recorded. Approximately 15 minutes after anesthetic induction, a valve was adjusted to switch the animal's breathing mixture from 79% $N_2$/21% $O_2$ to a predetermined mixture including CO (or, in control cases, a separate normal air mixture). Due to the logistics of preparing a large range of CO doses, pure CO was mixed with appropriate levels of compressed normal air, resulting in proportional decreases in both $N_2$ and $O_2$ partial pressures/composition percentages. Images were continually recorded for 60 minutes or until death, whichever came first.

Data procurement and analysis was done in an identical manner as for KCN-exposed animals. Briefly, streaming images were obtained, individual images were isolated from the streaming video, images were processed with basic DSP methods and then quantitatively analyzed for vessel coloration. Arteries and veins were identified and subsequently isolated based on characteristic presentation (caliber, location, etc.) and, when possible, A-V pairs (adjacent artery and vein) were evaluated to minimize any illumination-induced measurement errors. Digital signal processing methods used for these images were the same as those chosen for final implementation with KCN-exposed animals: (1) the color images were converted to gray-scale (0-255), (2) illumination characteristics were flattened, and (3) histogram equalization was employed to improve contrast in the color range which the vessels reside.

Figure 9:
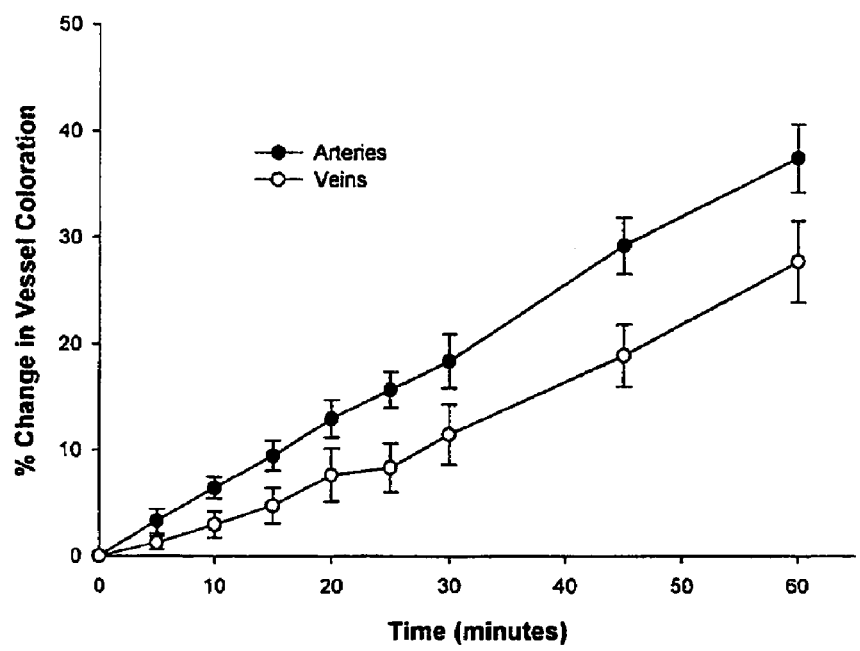
FIG. 9 shows the percent change in arterial and venous vessel coloration (normalized to control) in Sprague-Dawley rats in response to inhalational application of 3000 ppm CO over time, n=6. Changes in arterial and venous coloration became statistically significant (p<0.05) at the 15 minute and 30 minute time intervals, respectively.
Figure 12:
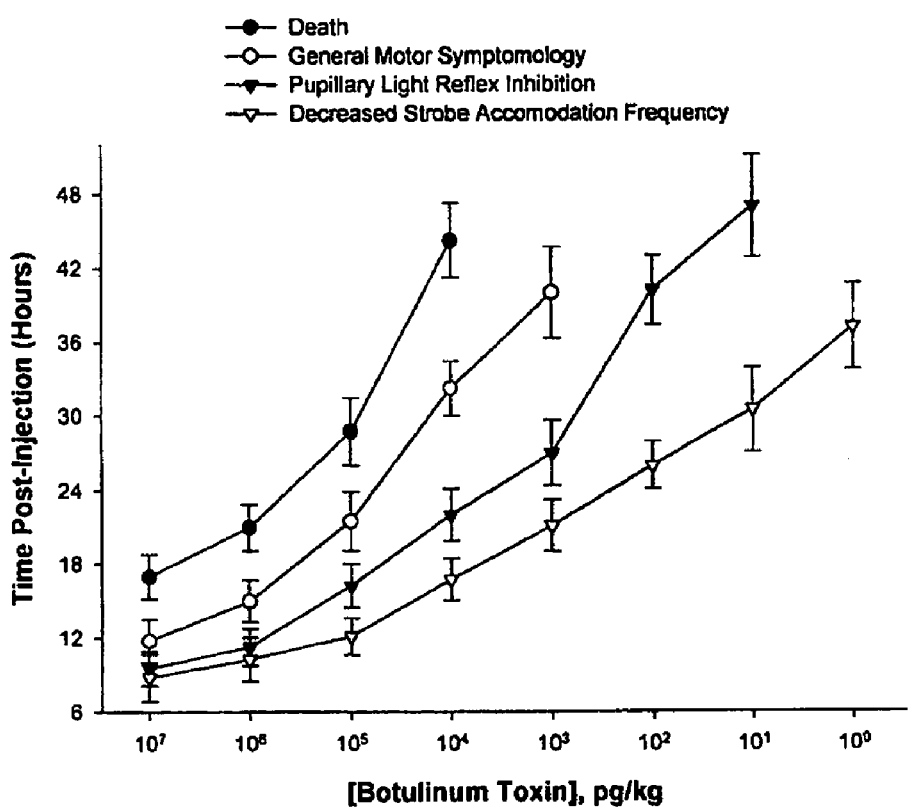
FIG. 12 is a concentration-response curves for Sprague-Dawley rats exposed to various concentrations of *botulinum* toxin, I.P. Data are plotted as means ±S.E.M. Data points which had means of greater than 48 hours are not plotted. X-axis ([*Botulinum* Toxin], pg/kg) is logarithmic and base-10 notation is used to indicate dose in picograms/kilogram. Loss of exploratory behavior was used for quantitation of general motor symptomology (see text). Significant (p<0.05) decrease in pupillary reflex to increased light intensity (compared to baseline) used to quantitate impaired pupillary reflex. See text for description of decreased strobe accommodation frequency. Decrease was indicated when value was significantly (p<0.05) less than control (i.e., 3.1 Hz or less). Note: larger X-axis values are at the left of the graph.

As the time course of vessel coloration change is examined in response to an approximate 60 minute $LD_{50}$ dose (3000 ppm), two characteristics become evident. Firstly, even at this high level of CO administration, the alteration in blood coloration is relatively gradual and linear. This fact is likely due to the route of administration and mechanism of action of CO. The change in coloration is proportional to the toxic load of CO, which increases in an approximate linear fashion with time. Secondly, statistically significant changes can be observed in both arterial (becomes significant at 15 minutes; $p<0.05$) and venous (becomes significant at 30 minutes; $p<0.05$) blood vessels. Interestingly, just as evidenced for the 3000 ppm dose in FIG. 9, significant changes in venous coloration trailed (occurred later in time) significant changes in arterial coloration at each concentration of CO which caused significant changes in both vessel types within the 60 minute application period (i.e., 60 minute doses of 500 ppm and greater). This indicates that a greater CO load is required to produce significant changes in venous blood coloration. This differential sensitivity to CO dosing may allow vessel coloration analysis to additionally indicate total CO load in addition to simply exposure vs. non-exposure.

Careful examination of the following CO dose-response curve provides additional information with respect to the functional diagnosis of CO inhalation. First, near maximal changes (92.3%) in arterial coloration were detectable in animals which did not expire within the 60 minute treatment period. Thus, either: (1) prolonged exposure to the maximal effects of CO are required prior to animal expiration, or (2) there is a threshold level in arterial oxygenation changes beyond which the present analytical methods cannot distinguish further changes in coloration. Secondly, statistically significant changes ($p<0.05$) were detected in animals which received 250 ppm CO for 60 minutes, 12-fold below $LD_{50}$ levels (3123 ppm). Unfortunately, this indication of a "diagnostic window" is not as indicative as it may be for other agents, for reason described above concerning exposure times. Though there is a twelve fold difference for the 60 minute exposure time, this ratio may likely vary as the exposure time is varied. However, based on the foregoing it can be noted with confidence that diagnosis of CO exposure is clearly obtainable at levels of exposure far less than lethal levels.

Example 5

Exposure to *Botulinum* Toxin

The first task was to determine the $LD_{50}$ for *botulinum* toxin. An initial survey of the literature as well as the internet (Centers for Disease Control, MSDS sheets, etc.) did not reveal the existence of prior determinations of the *botulinum* toxin $LD_{50}$ in rats. Therefore, preliminary dosing levels were based on the $LD_{50}$ reported for mice, 1 ng/kg. In the present study, employing intraperitoneal (I.P.) injection of *botulinum* toxin Type A, an extrapolated $LD_{50}$ of 2.28±0.97 ng/kg was obtained. If greater than 48 hours post-injection had been used as the endpoint for these experiments, this value would likely have been much lower. Many of the animals which received doses 10- to 30-fold lower than our 48 hour $LD_{50}$ (2.28 ng/kg) displayed advanced motor symptomology by the 48 hour post-injection time point, including decreased gross motor movements, jerky/uncoordinated movements, and labored breathing. Such signs were found to be consistent indicators of impending animal expiration. Even at the highest dose of *botulinum* toxin administered (30 µg/kg), over 68,000 times the 48 hour $LD_{50}$, animal expiration did not occur until at least 14 hours post-injection.

Regardless of dose, however, the onset and progression of symptoms followed a very similar and consistent pattern: initial increase in chewing behavior, decreased exploratory behavior, qualitative overall muscle weakness, jaw clenching and labored breathing, followed within hours by animal expiration. This was also evident with the initial ocular characteristic investigated, pupil motility. Thus, both the time of onset and the magnitude of pupil motility decrease were dependent upon the concentration of *botulinum* toxin administered. In order to determine the most appropriate time(s) to do the primary dose comparisons, the time course of changes in the pupillary light reflex and how such changes related temporally to the onset of other symptoms/death were investigated.

Sprague-Dawley rats were weighed, briefly anesthetized with halothane, and then administered the appropriate I.P. dose of Type A *botulinum* toxin (Metabiologics, Madison, Wis.). The toxin was diluted in saline to a concentration which allowed administration of between 0.2 and 1.0 ml of solution. Control animals were given 1 ml of saline I.P. in the same manner. Animals were subsequently tested for pupil size and pupillary light reflex in 1 hour increments post-injection in the same manner as in the parathion experiments discussed earlier. Briefly, animal pupils were monitored and recorded under very low light intensity conditions (1.7 $cd/m^2$). For pupillary light reflex measurements, the animals were subjected to "steps" in light intensity for response analysis. For each time point indicated, this involved 1 minute of high intensity lighting (80 $cd/m^2$) followed by return to baseline low level lighting intensity.

Figures 10, 11:
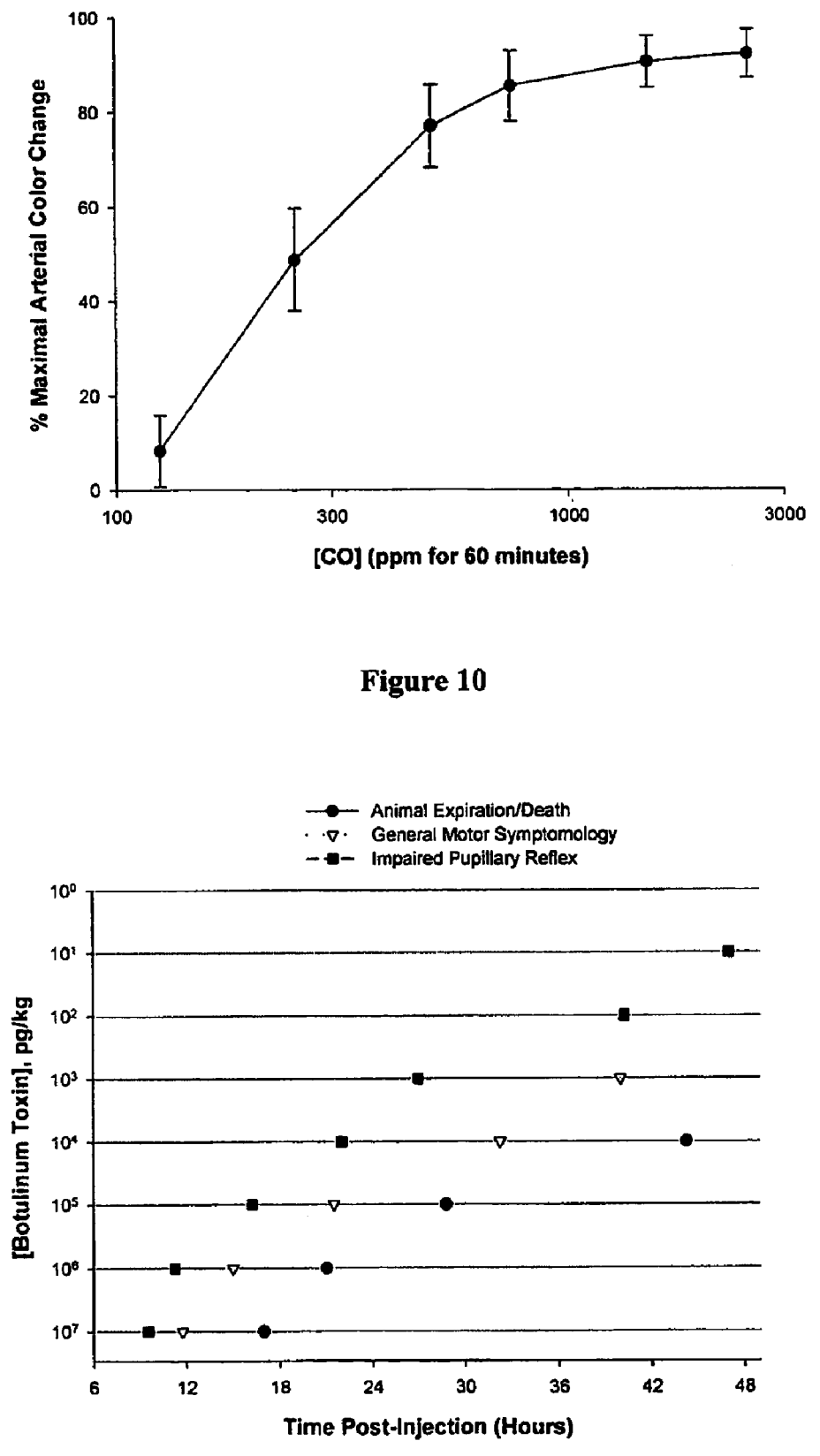

Experiments were designed and conducted in a "staggered" manner such that each animal was not actually tested for each of the 48 hours post-injection. Instead, by staggering the dosing schedule it was insured that there were sufficient numbers of animals at each dose to provide 4 measurements for each time point (hour) without the need for monitoring and testing each animal for a continual 48 hours. These time course data are presented in FIG. 11.

The most consistently observed generalized motor symptom was loss of exploratory behavior. This was descriptively quantified when an animal, upon being placed into a new cage for observation, did not move from the center location where it was placed within 1 minute. Turning/rotating movements were considered exploratory even if the animal remained in the center of the cage. A "positive" score for this test (i.e., no animal movement) was used to denote generalized motor symptomology. This test was performed hourly, just prior to ocular examinations.

Construction of a concentration-response curve for inhibition of the pupillary light reflex subsequent to *botulinum* toxin injection was not feasible for these experiments. Due to the highly varying rates of onset (i.e., onset occurs in low dose animals well after death occurs in high dose animals) a standard measurement time for which effects were near maximal in all animals was not obtainable. However, some indication as to the diagnostic capabilities of light reflex impairment may still be ascertained. In all animals which eventually expired, diminished pupillary light reflexes were detected. The time at which these deficits were detectable varied. The lowest *botulinum* toxin dose which resulted in statistically significant decreases in the pupillary light reflex was 10 pg/kg ($p<0.05$), 200-fold below the $LD_{50}$. Thus, it can be determined that the pupillary light reflex is a sensitive indicator (with regard to dose and time) of *botulinum* intoxication. It is, however, apparent that the ability to detect poisoning is highly dependent upon both the concentration of *botulinum* toxin administered as well as the length of time since administration.

In an attempt to enhance the diagnostic capabilities of pupil motility for the detection of *botulinum* toxin exposure a separate study was developed. The aim of these studies was to investigate whether physiological challenge of the pupillary light reflex with strobe lighting could more finely discern differences between exposed and non-exposed animals. In normal animals there is a maximal frequency at which the pupillary light reflex can function. This frequency is limited by the rate at which impulses denoting a light flash can travel from the retina, through the pupillary light reflex loop, and back to the muscles controlling pupil size for effect. In humans this maximal frequency is approximately 5 Hz (loop takes approximately 200 msec). The maximal frequency in normal Sprague-Dawley rats is about 3.48±0.57 Hz. Thus, significant decreases in the maximal response frequency after over-stimulation with high intensity light flashes can be indicate degradations along the reflex loop and may identify possible *botulinum* toxin exposure.

After pupil size and pupillary light reflex were tested during each time point as described above, the following protocol was used to examine the high intensity over-stimulation effect. Five minutes after conclusion of pupil size/reflex testing, the animal was subjected to a high intensity (90 cd/m$^2$) light flashing at a frequency of 1 Hz using a Grass photic stimulator tuned with universal counter-timer (Global Specialties Corporation). This frequency was incrementally stepped (0.1 Hz/step) every five seconds while continually recording pupillary fluctuations at 30 Hz via the video imaging system. Stepping continued until a frequency of 4 Hz was obtained (40 steps over 200 seconds). Preliminary studies indicated that 4 Hz was sufficiently above the maximal frequency at which normal rat pupils could respond to these light flashes. Data analysis then involved frame-by-frame analysis of the recorded images. The frequency at which the pupil ceased oscillating in size (in response to the intermittent flashes of light) and instead remained at a constant, fixed size as determined by the initial flash at a given frequency was determined to be the animals "cutoff" frequency. As noted above, this value for normal rats was 3.48±0.57 Hz.

The results of this study indicate that the experimental determination of a strobe cutoff frequency may be used for diagnostic determination of *botulinum* toxin exposure. However, much like earlier studies of the pupillary light reflex, the presentation time of these deficits were variable in relation to administered dose. As illustrated in the following Graph 11, the strobe cutoff frequency was temporally more sensitive than the normal pupillary light reflex test in diagnosing *botulinum* exposure (significantly more sensitive with concentration of 100 ng/kg and lower, p<0.05). Though this test of pupillary motility does increase the time window (prior to general symptomology and death) for diagnosis of *botulinum* toxin exposure, there remains the important variable of analysis time beyond that which exists for the other agents. Implementation of the described characteristics would require repeated diagnostic checks to insure that the observation time is not too soon after potential exposure. However, as with current clinical diagnosis, similar problems are likely to exist for any diagnostic evaluation of *botulinum* toxin exposure.

Example 6

Diagnosis of Exposure/Non-Exposure to Unknown

Due to administration and/or temporal characteristics unique to each agent, special care was taken to ensure the blinded validity of these studies. Since different routes of administration were necessary (parathion and *botulinum* toxin intraperitoneally, potassium cyanide subcutaneously, and carbon monoxide via inhalation) and different time points post-administration were used for data collection, 6 replicates of 3 concentrations of each agent as well as matched controls were used. This design preserved the ability to mask the data collector as to the predicted outcome (i.e., if only one dose of CO was used without matched controls, observer would know treatment based upon inhalational administration). Upon collection, data was given to a second experimenter who analyzed, without prior designation as to treatment, the data by transferring it to a Microsoft® Excel worksheet and running diagnostic macros. Use of these macros allowed automated analysis of the data, removing analytical judgment, bias, and/or error from the diagnostic determination. Data with animal diagnoses were then returned to the experimenter who knew the treatment (and level) for statistical analysis.

A flow chart illustrating an exemplary diagnostic pathway is presented in FIG. 1. The "cutoff" levels for the normal/control range were determined identically for each step. These ranges represent the control animal mean values ±2 standard deviations as determined during the experiments previously discussed. The blinded study included diagnostic evaluation of 100 Sprague-Dawley rats. Animals were administered test agent or control agent as detailed in Table 1, below.

TABLE 1

Animal composition for the blinded study.

| Parathion (intraperitoneal) | Potassium Cyanide (subcutaneous) | Carbon Monoxide (inhalation) | Botulinum Toxin (intraperitoneal) |
|---|---|---|---|
| 1 µg/kg (n = 6*) | 3 µg/kg (n = 6) | 250 ppm (n = 6) | 30 pg/kg (n = 6) |
| 10 µg/kg (n = 6) | 30 µg/kg (n = 6) | 750 ppm (n = 6) | 300 pg/kg (n = 6) |
| 1 mg/kg (n = 6) | 3 mg/kg (n = 6) | 3500 ppm (n = 6) | 3 ng/kg (n = 6) |
| 1 ml Corn Oil (n = 7)† | 1 ml Saline (n = 7) | Normal Air (n = 7) | 1 ml Saline (n = 7) |

*Number of animals at each concentration identified in parentheses.
†Bottom row lists the 4 control groups which were included (administered by same route as agent).

As noted in Table 1, three concentrations of each agent were included. These doses were chosen based on previous $EC_{50}$ and $LD_{50}$ determinations as well as minimal discernable effects. An approximate $LD_{50}$ dose was used for the highest dose, an approximate $EC_{50}$ dose (for the ocular characteristic) was used as the medium/mid dose, and a "minimal effect" dose was given as the lowest dose.

The diagnostic paradigm included two levels of evaluation: (1) diagnosis of exposure to a specific agent vs. non-exposed, and (2) if diagnosed as exposed, determination of the approximate level of exposure (low-, mid-, or high-level, corresponding to the three dosage levels). The first "level" of evaluation served as the primary test for ocular characteristic diagnostic validity to determine whether agents can be selectively indicated via ocular examination. The second "level" of evaluation provided an indicator of the sensitivity of the ocular characteristics for discerning gradations of exposure, as described above. Such capabilities may be valuable in mass casualty scenarios where both diagnosis of exposure type and level of need are important determinants. The results of the blinded, automated diagnosis of these animals are presented in Table 2.

TABLE 2

Results of automated diagnosis of animals from 4 treatment groups (parathion, potassium cyanide, carbon monoxide, botulinum toxin) and matched controls including 3 subgroups for each agent.

| Exposure & Level | Correct Agent Diagnosis/Total (%) | Correct Agent and Level Diagnosis/Total (%)* |
|---|---|---|
| Control | 28/28 (100%)# | N/A |
| 1 ml Corn Oil (i.p.) | 7/7 (100%) | N/A |
| 1 ml Saline (s.c.) | 7/7 (100%) | N/A |
| Normal Air Inhaled | 7/7 (100%) | N/A |
| 1 ml Saline (i.p.) | 7/7 (100%) | N/A |
| Parathion (i.p.) | 16/18 (89%) | 16/18 (89%) |
| 1 µg/kg | 4/6 (67%) | 4/6 (67%) |
| 10 µg/kg | 6/6 (100%) | 6/6 (100%) |
| 1 mg/kg | 6/6 (100%) | 6/6 (100%) |
| Potassium Cyanide (s.c.) | 15/18 (83%) | 14/18 (78%) |
| 3 µg/kg | 3/6 (50%) | 3/6 (50%) |
| 30 µg/kg | 6/6 (100%) | 5/6 (83%) |
| 3 mg/kg | 6/6 (100%) | 6/6 (100%) |
| Carbon Monoxide (inhaled) | 16/18 (89%) | 15/18 (83%) |
| 250 ppm | 4/6 (67%) | 3/6 (50%) |
| 750 ppm | 6/6 (100%) | 6/6 (100%) |
| 3500 ppm | 6/6 (100%) | 6/6 (100%) |
| Botulinum Toxin (i.p.) | 12/18 (67%) | 11/18 (61%) |
| 30 pg/kg | 0/6 (0%) | 0/6 (0%) |
| 300 pg/kg | 6/6 (100%) | 6/6 (100%) |
| 3 ng/kg | 6/6 (100%) | 5/6 (83%) |
| TOTALS | 87/100 (87%) | 56/72 (78%) |

*Indicates proportion of animals correctly diagnosed with respect to both the agent and the level of agent.
Proportion and percentage for all levels of a given agent exposure All non-exposed, mid-level-exposed, and high-level-exposed animals were correctly diagnosed with respect to agent (76 of 76, 100%). Of these, only 2 animals were misidentified with respect to exposure level (1 mid-level KCN-exposed diagnosed as low-level KCN exposure and 1 high-level *botulinum* toxin-exposure animal diagnosed as mid-level *botulinum* exposure). All fully missed diagnoses were at low levels of agent, with the many of these (6 of 13 total, 46%) being low-level *botulinum* toxin-exposed animals. The portion (11 of 24, 46%) of the low-level-exposed animals which were correctly diagnosed with respect to exposure was much greater than was anticipated. The concentrations of the various agents used for these low-level exposures were below levels which caused significant changes during the experiments previously discussed. Thus, the fact that nearly half of these animals were correctly diagnosed indicates a greater level of diagnostic sensitivity than was expected. In addition, analysis of the statistical data from the blinded study indicates that the paradigm used to make the diagnostic decisions may be improved for greater discernment of the low-level agents. In particular, an increased incorporation of low-light pupil size and the pupillary light reflex data into the *botulinum* toxin diagnosis may enhance our ability to correctly identify animals exposed to low levels of this agent.

CONCLUSION

While various embodiments of the present invention have been described above, it should be understood that they have been presented by way of example only, and not limitation. It will be understood by those skilled in the art that various changes in form and details may be made therein without departing from the spirit and scope of the invention. Thus, the breadth and scope of the invention should not be limited by any of the above-described exemplary embodiments.

What is claimed is:

1. A method of diagnosing cyanide exposure of a subject, comprising the step of:
    (a) determining whether the subject's ocular blood vessel coloration varies significantly from a normal ocular blood vessel coloration by:
        (1) quantifying the subject's ocular blood vessel coloration; and
        (2) comparing the quantity from said step (1) to a quantified normal vessel coloration.

2. The method of claim 1, wherein the normal ocular blood vessel coloration of said step (a) is determined for each subject.

3. The method of claim 1, wherein the normal ocular blood vessel coloration of said step (a) is determined as an average for a population to which the subject belongs.

4. The method of claim 1, wherein the ocular blood vessels of said step (a) are venous vessels.

5. The method of claim 1, wherein the ocular blood vessels of said step (a) are arterial vessels.

6. A method of diagnosing carbon monoxide exposure of a subject, comprising the step of:
    (a) determining whether the subject's ocular blood vessel coloration varies significantly from a normal ocular blood vessel coloration by:
        (1) quantifying the subject's ocular blood vessel coloration; and
        (2) comparing the quantity from said step (1) to a quantified normal vessel coloration.

7. The method of claim 6, wherein the normal ocular blood vessel coloration of said step (a) is determined for each subject.

8. The method of claim 6, wherein the normal ocular blood vessel coloration of said step (a) is determined as an average for a population to which the subject belongs.

9. The method of claim 6, wherein the ocular blood vessels of said step (a) are venous vessels.

10. The method of claim 6, wherein the ocular blood vessels of said step (a) are arterial vessels.

11. A method of diagnosing botulinum toxin exposure of a subject, comprising the step of:
    (a) determining whether the subject's strobe cutoff frequency varies significantly from a normal strobe cutoff frequency by:
        (1) quantifying the subject's strobe cutoff frequency; and
        (2) comparing the quantity from said step (a1) to a quantified normal strobe cutoff frequency.

12. The method of claim 11, wherein the normal strobe cutoff frequency of said step (a) is determined for each subject.

13. The method of claim 11, wherein the normal strobe cutoff frequency of said step (a) is determined as an average for a population to which the subject belongs.

* * * * *